(12) United States Patent
Shankar

(10) Patent No.: US 8,197,416 B1
(45) Date of Patent: Jun. 12, 2012

(54) PULSATILE MEASUREMENT OF CARDIAC MALFUNCTION CONDITIONS

(76) Inventor: Ravi Shankar, Boca Raton, FL (US)

( * ) Notice: Subject to any disclaimer, the term of this patent is extended or adjusted under 35 U.S.C. 154(b) by 1558 days.

(21) Appl. No.: 11/507,629

(22) Filed: Aug. 21, 2006

Related U.S. Application Data

(60) Provisional application No. 60/709,596, filed on Aug. 19, 2005.

(51) Int. Cl.
*A61B 5/02* (2006.01)

(52) U.S. Cl. ......... 600/492; 600/490; 600/494; 600/482

(58) Field of Classification Search .......... 600/490–499, 600/481, 483–485, 507, 547; 606/200–202
See application file for complete search history.

(56) References Cited

U.S. PATENT DOCUMENTS

| | | | |
|---|---|---|---|
| 3,835,840 A * | 9/1974 | Mount | 600/506 |
| 4,144,878 A * | 3/1979 | Wheeler | 600/506 |
| 5,241,963 A | 9/1993 | Shankar | |
| 5,297,556 A | 3/1994 | Shankar | |
| 5,343,867 A | 9/1994 | Shankar | |
| 5,630,424 A | 5/1997 | Raines | |
| 5,718,232 A | 2/1998 | Raines | |
| 6,017,307 A | 1/2000 | Raines | |
| 6,149,587 A | 11/2000 | Raines | |
| 6,152,881 A | 11/2000 | Raines | |
| 7,316,652 B2 * | 1/2008 | Dalgaard et al. | 600/499 |
| 2005/0228302 A1 * | 10/2005 | Dalgaard et al. | 600/499 |

OTHER PUBLICATIONS

Bonetti, P.O., et al., Enhanced External Counterpulsation for Ischemic Heart Disease, Journal of the American College of Cardiology, vol. 41, No. 11, 2003, pp. 1918-1925.

CRC, CRC Handbook of Chemistry and Physics, 62nd Edition, CRC Press, 1982, pp. F-11, F-12, and F-49.

Doobay, A.V., and Anand, S.S., Sensitivity and Specificity of the Ankle-Brachial Index to Predict Future Cardiovascular Outcomes, Arterioscler. Thromb. Vascu. Biol., Jul. 2005.

Doebelin, E.O., Measurement Systems, 4th Edition, McGraw-Hill, 1990, pp. 124, 125.

Faxon, D.P., Creager, M.A., et al., Atherosclerotic Vascular Disease Conference: Executive Summary, Circulation, vol. 109, Jun. 1, 2004, pp. 2595-2604.

Herrington, D. et al., "Relationship Between Arterial Stiffness and Subclinical Aortic Atherosclerosis," Circulation, vol. 110, pp. 432-437, Jul. 27, 2004.

Kolluri, S., and Shankar, R., "Noninvasive Det. Of Atherosclerosis Using the Imp. Plethysmograph," World Congress Med. Phys. and Biomed. Engr, Osaka, Japan, Jul. 1991.

Lerman, A., and Zeiher, A.M., Endothelial Function, Contemporary Reviews in Cardiovascular Medicine, Circulation, vol. 111, pp. 363-368, 2005.

Milnor, W.R., Hemodynamics, 2nd Edition, Williams & Wilkins, Baltimore, MD, 1989.

Mitchell, G.F., Parise, H., et al., Local Shear Stress and Brachial Artery Flow-Mediated Dilation: The Framingham Heart Study, Hypertension, vol. 44, Aug. 2004, pp. 134-139.

(Continued)

*Primary Examiner* — Navin Natnithithadha

(74) *Attorney, Agent, or Firm* — Alvin S. Blum

(57) ABSTRACT

Apparatus includes at least one of inflatable blood pressure cuffs for encircling a proximal, a distal, and an intermediate portion of a limb. Electrical signals from a pressure transducer on the cuff and from skin contact electrodes on the cuff are generated during pulses from the heart or from externally generated cuff pulses. A signal processing mechanism generates numerical values that are relevant to conditions that may contribute to cardiac malfunction.

19 Claims, 10 Drawing Sheets

OTHER PUBLICATIONS

Naghavi, M., et al., From Vulnerable Plaque to Vulnerable Patient: A Call for New Definitions and Risk Assessment: Part I, Circulation, vol. 108, Oct. 7, 2003, pp. 1664-1672.

Naghavi, M., et al., From Vulnerable Plaque to Vulnerable Patient: A Call for New Definitions and Risk Assessment: Part II, Circulation, vol. 108, Oct. 14, 2003, pp. 1772-1778.

O'Rourke, M., Safar, M., and Dzau, V., Eds, Arterial Vasodilation: Mechanisms and Therapy, Lea & Febiger, Philadelphia, 1993.

Rubanyi, G.M, in Flow-Dependent Regulation of Vascular Function, J.A. Bevan, et al, editors, Oxford Univ. Press, NY, 1995, Chapter 6, pp. 119-127.

Shankar, T.M.R., The Origin of Impedance Pulse in the Limbs and Arterial Compliance Studies, Ph.D. Dissertation, , University of Wisconsin, Madison, WI, 1982.

Shankar, R., and Webster, J.G., "Noninvasive Measurement of Compliance of Human Leg Arteries," IEEE Trans. Biomed. Eng., vol. 38, No. 1, pp. 62-67, Jan. 1991.

Shankar, T.M.R., and Webster, J.G., "Noninvasive Determination of Arterial Volume-Pressure Curve," Paper 41.5, 37th ACEMB, Los Angeles, Sep. 1984.

Shankar, R.,, and Bond, M.G., "Correlation of Noninvasive Arterial Compliance with Anatomic Pathology," Atherosclerosis, vol. 85, pp. 37-46, Dec. 1990.

Shankar, T.M.R., et al., "The Contribution of Vessel Volume Change and Blood Resistivity Change," IEEE Trans. Biomed. Eng., vol. BME-32, No. 3, pp. 192-198, Mar. 1985.

Shankar, T.M.R., and Webster, J.G., "Contribution of Different Sized Vessels in the Extremities," Med. Biol. Eng. Comput.,. vol. 23, pp. 155-164, Mar. 1985.

Shankar, T.M.R., and Webster, J.G., "Design of an Automatically Balancing Electrical Impedance Plethysmograph," Journal of Clin. Eng., vol. 9, pp. 129-134, Apr.-Jun. 1984.

UPMC, Nitroglyercin Patch, University of Pittsburgh Medical Center, Information for Patients, 1996.

Warren, J.B., Ed, The Endothelium, Wiley-Liss, New York, 1990, p. 113.

Webster, J.G., Ed, Medical Instrumentation, 3rd Edition, John Wiley & Sons, Inc., New York, 1998.

Deloughery, T.G., Hemostasis & Thrombosis, Landes Biosciences, Austin, 1999.

Dormandy, J.A., Medical and engineering problems of blood viscosity, Biomedical Engineering, Jul. 1974, 284-303.

Hathcock, J.J., Flow Effects on Coagulation and Thrombosis, Arterioscler Thromb Vasc Biol, Aug. 2006, vol. 26, pp. 1729-1737.

Junker, R., et al., Relationship between plasma viscosity and the severity of coronary heart disease, Arteriosclerosis Thrombosis Vascular Biology, vol. 18, 1998, pp. 870-875.

Koenig, W., et al., Plasma Viscosity and the risk of Coronary Heart Disease, Arteriosclerosis Thrombosis Vascular Biology, vol. 18, 1998, pp. 768-772.

Turgeon, M.L., Clinical Hematology, 2nd Edition, Little, Brown and Company, Boston, 1993.

* cited by examiner

Figure 7
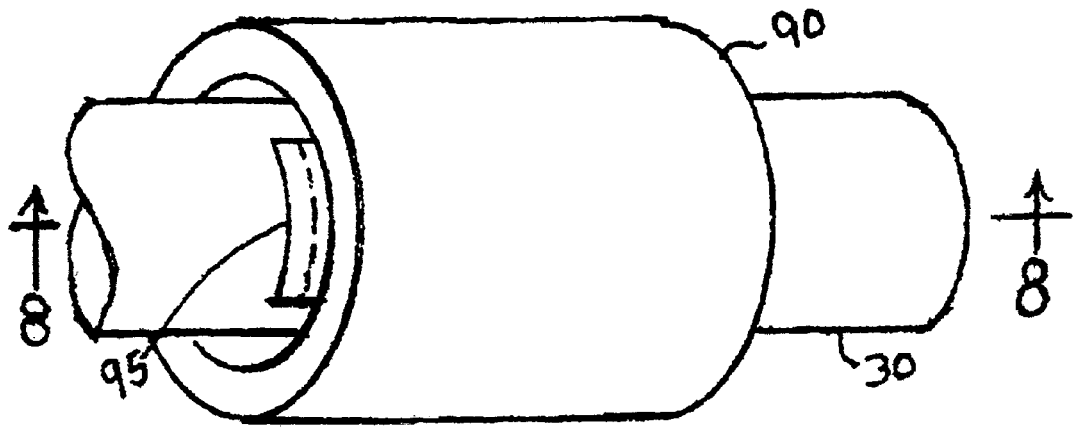
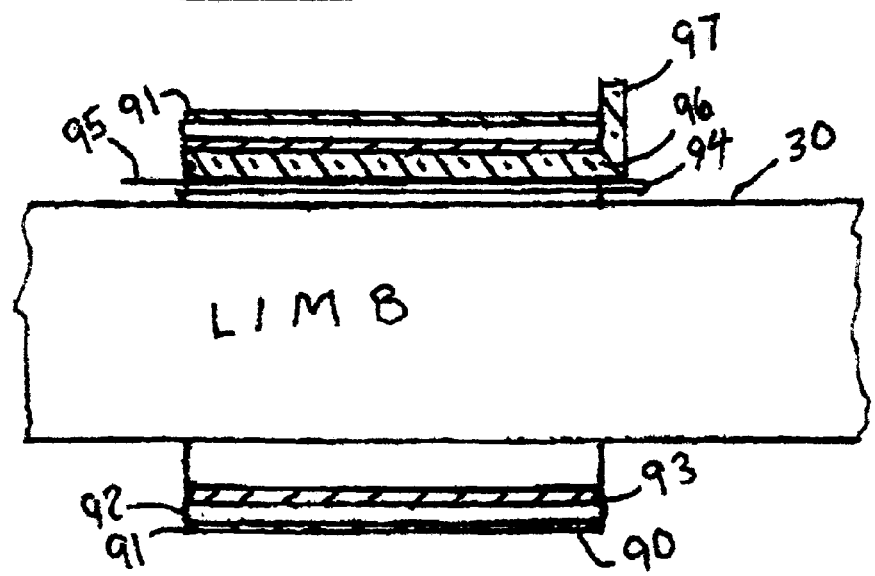
Figure 8

PULSATILE MEASUREMENT OF CARDIAC MALFUNCTION CONDITIONS

This application claims the benefit of Provisional Patent Application No. 60/709,596, filed 2005 Aug. 19, entitled "mechanical pulsations for diagnostics of a person vulnerable to sudden cardiac death" incorporated herein by reference.

BACKGROUND

This invention relates to noninvasive monitoring of conditions that may contribute to cardiac malfunctioning by pulsatile measurements in a limb.

Many people die suddenly of heart disease without prior symptoms. A recent consensus definition of a vulnerable patient has been evolved by medical professionals to identify people prone to sudden cardiac death [Naghavi, et al., 2003]. The definition provides a framework to combine the risks due to the formation of plaques in the blood vessels ("Vulnerable Plaque"), blood clots ("Vulnerable Blood"), and failing heart musculature ("Vulnerable Myocardium"). They define a vulnerable plaque as a future culprit plaque. It denotes the likelihood of having a cardiac event in the future. They recommend a combination of structural and functional methods for plaque characterization as this may provide higher predictive value than a single approach. However, they primarily catalogue structural methods, for use on coronary and carotid arteries. Arteries in the lower leg can be an effective substitute to evaluate the disease extent [Faxon and Creager, 2004] as atherosclerosis is a systemic disease. Available diagnostic methods characterize plaques into three categories: structural, regulatory, and functional.

Shankar [U.S. Pat. Nos. 5,343,867; 5,297,556; and 5,241,963] developed a functional measure, related to maximal compliance of the artery, a measure of relative contents of elastin and collagen in the artery. It is significantly less expensive to perform, and more sensitive, especially for pre-clinical atherosclerosis; however, it is slow, requires a separate measurement of blood pressure, and does not fully exploit the potential dynamic range. Current methods of blood pressure measurement also have observer and process errors.

Raines' Patents [U.S. Pat. Nos. 6,149,587; 5,630,424; and 5,718,232] added automated calibration to a chamber (or air or mechanical) plethysmograph (plethysmographs measure changes in volume) and measured near-maximal compliance of the artery, and combined with several other measures, such as ABI (Arm-Brachial Index) and Framingham risk profile (FRP). Raines also [U.S. Pat. No. 6,152,881] used reactive hyperemia to "activate" the endothelium and measure maximal compliance in the arm under FMD conditions.

EECP (enhanced external counterpulsation) is a last resort method that aids an ischemic heart with inflatable cuffs that are wrapped around the patient's legs at the calves and at the lower and upper thighs [Bonetti, et al., 2003]. A computer-guided device inflates and rapidly deflates them, sequentially, during diastole. That aids venous return to the heart and provides symptomatic relief. However, the method would not be useful for peripheral hemodynamic evaluation and is primarily used to substitute and enhance the effectiveness of venous pressure stockings.

This invention also uses the same apparatus to detect propensity towards inappropriate internal blood clotting in a vulnerable patient. This invention exploits pathological changes in blood viscosity to obtain pulsatile methods with large dynamic range. High blood viscosity results from increased fibrinogen and platelet counts (Blood factors involved in clot formation), higher number of white blood cells (which increase during infection and inflammation), increased number of red blood cells, and reduced deformability of red blood cells. All these changes can occur during the atherosclerotic disease progression, and can speed up prior to an acute event of injury or death of heart muscle tissue. Thus, high blood viscosity is a simple and sensitive indicator of internal blood clotting. Blood viscosity is currently measured using blood drawn from the person, by quantifying certain blood markers, such as fibrinogen and D-Dimer, at a high shear rate [DeLoughery, 1999; Turgeon, 1993]. Shear rate is a measure of the velocity gradient across the lumen of a vessel. At low shear rates red blood cell aggregation occurs and in-vitro (outside the body) techniques (unpublished) to uncover this may be under development [Hathcock, 2006]. Viscosity is asymptotically constant at high shear rates [Dormandy, 1974] and may show a dynamic range of 10 with shear rates [Hathcock, 2006]. Stagnant blood, however, is more susceptible to clotting, has higher viscosity, and has a wider separation between persons who are healthy and atherosclerotic. Plasma viscosity, as well as fibrinogen and WBC (white blood cell) counts, is positively associated with coronary heart disease (CHD) events [Koenig et al., 1998]. Furthermore, a positive relationship between plasma viscosity and the severity of CHD has been shown [Junker et al., 1998]. Venous Occlusion Plethysmography [Webster, 1998] is a noninvasive technique that can evaluate thrombosis (internal clots) in veins.

SUMMARY

This invention provides for early diagnosis and management of conditions that contribute to cardiac malfunction. It includes measurements that can be used seamlessly from early mass screening to eventual post-intervention follow-up of cardiac malfunction. This invention uses an externally generated pressure pulse, or the patient's blood pressure pulse, to obtain these measurements. The measurements are noninvasive, simple, inexpensive, rapid, objective, and accurate. Different combination of these measurements allows one to trade off sensitivity against specificity. This invention provides measurements for vulnerable plaque, vulnerable blood, and vulnerable myocardium, so an integrated measurement can be developed to diagnose vulnerable patients; and to monitor them and manage them during and after medical and other interventions. These measurements may be applied to diabetes management.

The object of this invention is to provide a method that is reproducible; and readily applicable to an asymptomatic population, and capable of adding predicted value to measurements of established risk factors; Naghavi, et al identify the need for such a method. It is a further object to provide a cost-effective, step-wise approach designed to further stratify risk and provide reliable diagnosis and pathways for monitoring therapy.

It is another object to combine local hemodynamic factors (functional and regulatory measurements) and morphology (structural measurements) to provide insight regarding the temporal course of conditions contributory to cardiac malfunction.

It is a further object to use pulsatile signals, both external and physiological, to produce these measurements.

It is a further object to obtain high specificity by isolating a specific effect, such as that of vascular smooth muscle via vasoconstriction or vasodilatation with peripheral application of transdermal patches or limb exercises It is a further object to obtain blood pressure measurements, that are more accurate and repeatable, and less prone to observer error, with the aid of a stiff cuff.

It is an object of the present invention to provide at least one cuff selected from the group consisting of
- a proximal blood pressure cuff with inflatable bladder and cuff pressure system for encircling a proximal portion of the limb,
- a distal pressure cuff with inflatable bladder and cuff pressure system for encircling a distal portion of the limb, and
- an intermediate pressure cuff with inflatable bladder and cuff pressure system for encircling a portion of the limb intermediate to the proximal and distal portions;
- at least one of the cuff pressure systems provided with means to generate external pressure pulses, with means to time the pressure pulses to occur during diastolic phase of the person's blood pressure pulse;
- at least one of the pressure cuffs connected to a pressure bulb, a release valve, and an analog pressure gauge with an electronic pressure transducer providing electric signals indicative of pressure, with means for appropriate calibration;
- whereby mechanical plethysmographic measurements are made on output signals from pulse pressure;
- at least one of said pressure cuffs having four aluminum electrodes on the inside of the cuff, with electrical leads connected to the four electrodes, with said electrical leads providing electric plethysmographic output signals from pulse pressure; and
- signal processing means connected to the electric plethysmographic output signals and pressure transducer output signals from said pulse pressure for computing and displaying values relevant to conditions contributory to cardiac malfunction.

It is an object of this present invention to provide several noninvasive measurements for characterizing the propensity for internal blood clotting (vulnerable blood), with the apparatus. It is a key object to utilize changes in viscosity with shear rate and atherosclerotic disease, which may be hundred fold, to develop multiple methods.

Further objects and advantages of my invention will become apparent from a consideration of the drawings and ensuing description.

BRIEF DESCRIPTION OF DRAWINGS

FIG. 7 is a perspective view of a cuff with a vasoactive pad of the invention.

FIG. 8 is a sectional view taken through line 8-8 of FIG. 7.

DETAILED DESCRIPTION OF THE INVENTION

Figure 1:
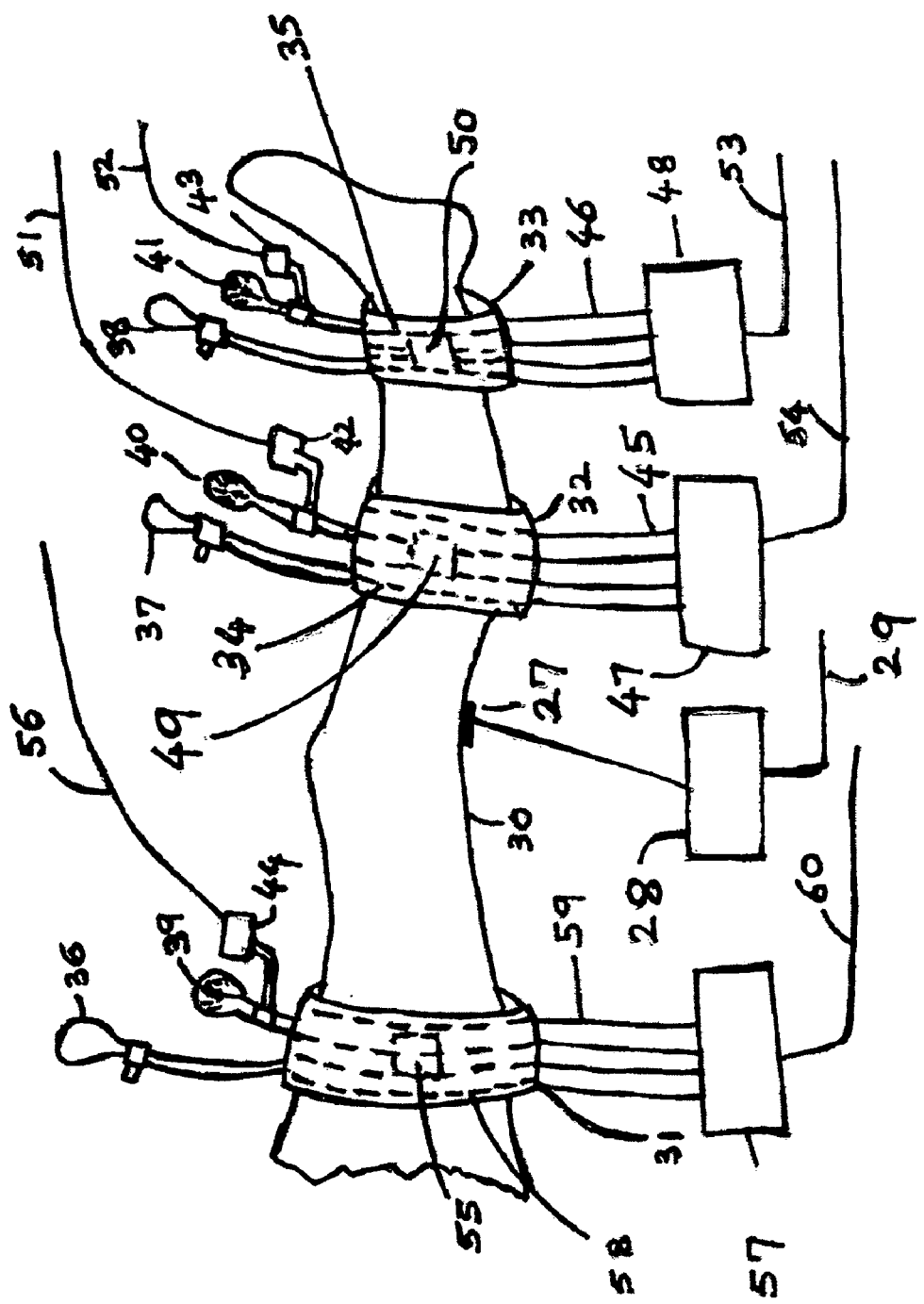
FIG. 1 is a perspective view of apparatus of the invention on a limb.

Referring now to FIG. 1, the HEART PULSE apparatus of the invention includes three cuffs, 31, 32 and 33, with inflatable bladders and cuff pressure systems 36, 37, 38, that encircle the leg 30 of a person (they may also be used on an arm, but a leg is preferred). The Proximal cuff 31 is closest to heart. Distal cuff 33 is farthest from heart. Intermediate cuff 32 is between the proximal and distal cuffs.

Any or all of the three cuffs may be adapted for use as an electrical plethysmograph (EP) to measure electrical property change at the limb under the cuff as a pulse passes. EP is also called an impedance plethysmograph. An electrical plethysmograph uses either 2 or 4 aluminum electrodes, 58, 34 and 35, that are affixed at equal spacing on the inside of a conventional cuff. The current source is typically 10 mA rms at a frequency of 100 KHz, which is fed through the two outer electrodes, while the two inner electrodes are uses as voltage sensing electrodes. The electrodes are connected by electrical lead sets 59, 45, and 46 to electrode instruments 57, 47 and 48, to generate the current and process the sensed voltage signals, respectively for the proximal, intermediate, and distal cuffs. These instruments convert the respective 100 KHz voltage signals to electrical signals that are termed here as Electrical Limb Pulse (ELP) signals, 60, 53 and 54, respectively for the three cuffs. This ELP signal, obtained as the ratio of voltage to current, has both an ac ($\Delta R$) and a dc (R) component. The latter corresponds to the tissue volume (per unit length), while the former corresponds to the limb volume changes, which can be computed as $-\rho \times L \times (\Delta R)/R^2$, where $\rho$ is the blood resistivity and L is the length of the limb segment under the cuff Any or all of the three cuffs may be adapted for use as a mechanical plethysmograph (MP) to measure volume changes in the limb segment under the cuff. MP is also called a volume, air, or chamber plethysmograph Pressure transducer assemblies 44, 42 and 43 convert the corresponding cuff pressure signals to electrical signals that are termed Mechanical Limb Pulse (MLP) signals, 56, 51 and 52, respectively for the proximal, intermediate, and distal cuffs. These signals have both an ac ($\Delta P$) and a dc pressure (P) component. The latter measures the dc cuff pressure. The former, given the volume of the cuff, V, can be converted to read limb volume change, $\Delta V$, as $\Delta P \times V/P$. However, since V is not easily measured, it is routine practice to introduce a 1 ml calibration signal at different cuff pressures and measure pressure change (PC). PC is the calibration constant for that cuff pressure P; one can obtain the corresponding volume change $\Delta V$ by dividing measured $\Delta P$ with PC. Both EP and MP are in common clinical use.

Proximal cuff 31 may be inflated to different pressures by pressure assembly 36, with the pressure read on pressure gage 39. In addition to its use as a plethysmograph, it may also be used to block venous return, for reactive hyperemia, or for isolating the limb segment distal to the cuff. A bio-chemically impregnated transdermal patch 55 may also be used under the cuff 31 to administer a drug to cause local vasoconstriction or vasodilatation. The intermediate cuff 32 is inflated to different cuff pressures by pressure bulb assembly 37, with the pressure read on pressure gage 40. It may also serve purposes similar to the proximal cuff. A bio-chemically impregnated transdermal patch 49 may also be used under the cuff 32 to cause local vasoconstriction or vasodilatation. Distal Cuff 33 is typically used to estimate a correction factor for the pressure pulse height, so the measurements measured are more accurate. It is inflated to a low cuff pressure of about 20 to 30 mm Hg by pressure bulb assembly 38, with the pressure read on pressure gage 41. A bio-chemically impregnated transdermal patch 50 may also be used under the cuff 33 to cause local vasoconstriction or vasodilatation. Distal Cuff 33 may also be inflated to a high pressure to block blood flow out of the limb segment. Ultrasonic transducer 27 is shown applied on the underside of the leg and is used to measure blood flow in a major limb blood vessel with the aid of ultrasonic flowmeter 28 which provides an electrical signal 29 for further processing.

Figure 5:
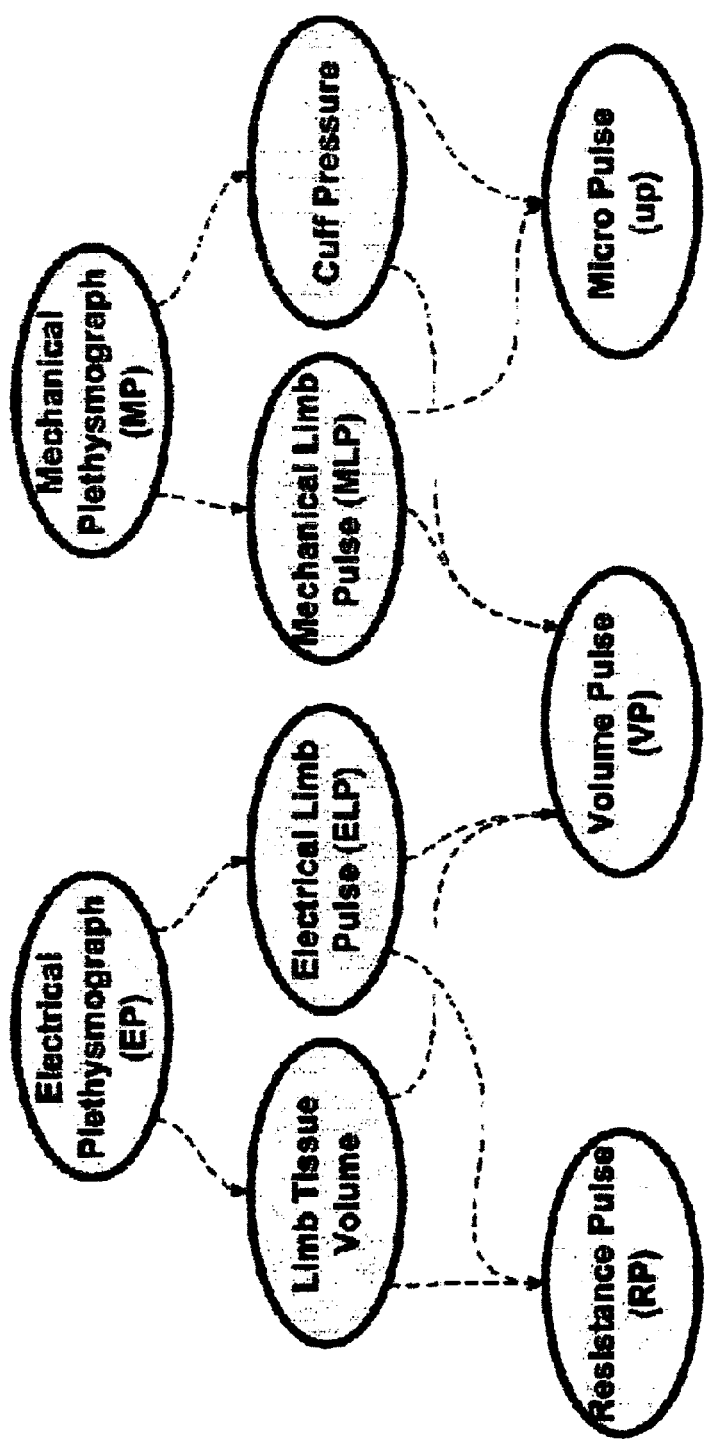
FIG. 5 shows the different plethysmographic instruments used and pulse signals obtained from them.

The limb volume change measured is the signal generated as a consequence of the blood pressure pulse (BPP) that travels down the arteries from the heart, propelling blood forward. A plethysmograph, by definition, measures volume change; however because of the transduction process, it may include other contributions. Assume both ELP and MLP signals are obtained from the same limb segment. See FIG. 5. The ELP signal from an electrical plethysmograph EP, has two major contributions, due to arterial volume changes, labeled here as Volume Pulse (VP), and due to arterial blood resistivity changes, labeled here as Resistance Pulse (RP). The MLP signal recorded from a mechanical plethysmograph has two major contributions, due to arterial volume changes, labeled already as Volume Pulse VP, and due to microcirculatory volume changes, labeled here as Micro Pulse (uP). Under normal conditions, the limb pulses recorded from electrical and mechanical plethysmographs, ELP and MLP, track each other in shape and amplitude, since Volume Pulse VP is the major contributor to both. However, this may change under various conditions of stress and disease. For this invention, Volume Pulse VP is of primary concern, and thus methods of this invention are designed to accentuate this contribution from these plethysmographs.

Both plethysmographs may incorporate automatic calibration mechanisms well known in the art. Calibration for an electrical plethysmograph is easy and independent of patient setting. The mechanical plethysmograph requires a minimum pressure of 20 to 30 mm Hg to make good contact with the skin and may have to be calibrated for each use. Both manual and automatic calibration schemes exist. A simple manual calibration procedure for a mechanical plethysmograph would be to introduce 1 ml into the pressure cuff and noting the change in pressure.

Figure 2:
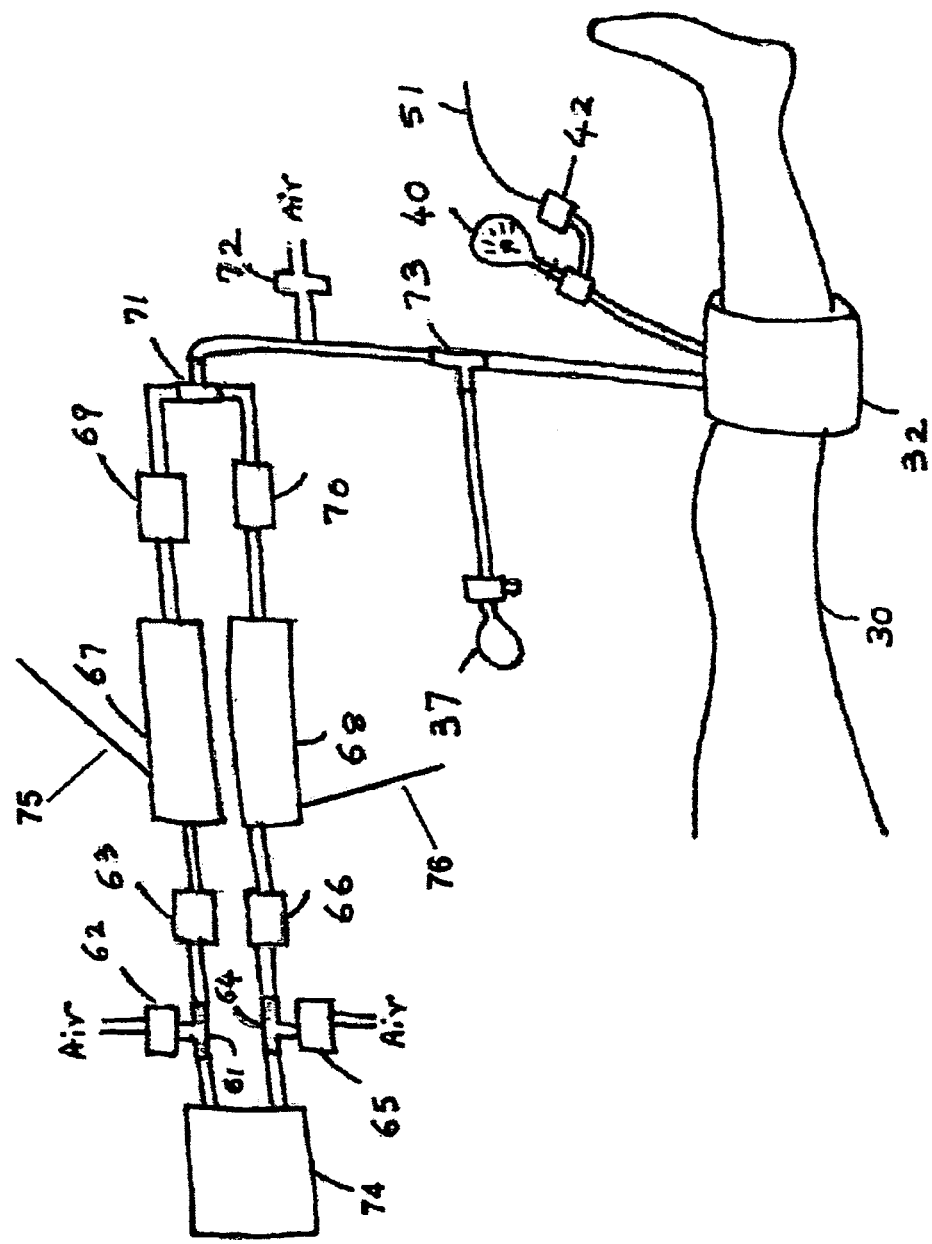
FIG. 2 is a perspective view of another embodiment of the invention with external pulse generator.

FIG. 2 represents the preferred embodiment, HEARTLESS PULSE, where the pressure pulse applied to the limb segment under the intermediate cuff is generated locally and externally; in this invention, it is called LPP, for local pressure pulse; LPP is generated with a suitable pump 74 to serve two different purposes: SET PRESSURE option: automatically inflate, Auto_Inflate, and automatically deflate the cuff, Auto_Deflate, at a slow rate of 2 to 3 mm Hg/second, and hold, Auto_Hold, the pressure at intermediate cuff pressures; and the GENERATE PULSE option: for generation of external pressure pulses, of different periods and amplitudes, and for computer controlled application. The SET PRESSURE functions are accomplished with a Y-tube 61 that connects the pump to air via solenoid valve 62 and to a computer adjustable orifice 67 via solenoid valve 63. The other side of 67 is connected to solenoid valve 69 which connects to one end of the Y-tube. The GENERATE PULSE functions are accomplished, similarly, with a Y-tube 64, to air via solenoid valve 65, and to a computer controlled orifice 68 via a solenoid valve 66. The computer controlled orifices are expected to be about 10 cm long, with a radius range of 0.1 to 1 cm, adjusted under computer controls 75 and 76, to generate different square pressure pulses, as needed. The other end of 68 is connected to a solenoid valve 70 which connects to another end of the Y-tube 71. The pump is attached to the intermediate cuff via a Y-tube 73 and another Y-tube 71 to connect two paths of tubing and different valves, one for each of the above suites of specified functions. Pressure transducer 42 provides information on pressure to a computer-based controller which controls the operation of the solenoid valves and the pump, as well as the computer controlled orifices. A safety valve 72 is connected to the tubing between 71 and 73 to release the pressure in the bladder in case it is held at a high pressure (250 mm Hg or above) for more than a few seconds. Computer Controlled Orifice 67 allows a pressure increment of 10 mm Hg in the cuff to be reached in 2 to 3 seconds. Computer adjusted orifice 68 is designed to yield single pulses with amplitudes of 5 to 40 mm Hg, and periods of 200 ms to 600 ms, timed to occur during diastole, and for up to 20 seconds when the limb segment is isolated with a proximal cuff, depending upon the application. GENERATE PULSE functions may be subdivided into two categories: Generation of the step function, HEARTLESS STEP, and Generation of the square pulse, HEARTLESS SQUARE. HEARTLESS STEP is used to measure the compliance of the limb artery segment, without the need for either electrical or mechanical plethysmograph. The compliance is deduced by noting the time for the pressure to reach the full value, and knowing a priori the resistance and inertance of the computer adjustable orifice. HEARTLESS SQUARE is used for stressing the local limb segment as well as for computing compliance, in conjunction with an electrical plethysmograph. This is the default option of GENERATE PULSE function. Let p be the pressure pulse amplitude applied, and v the volume change measured by the plethysmograph. Then, the compliance is computed as v/p. By keeping p low, say 5 to 10 mm Hg, compliance averaging as with HEART PULSE is avoided. The pulse amplitude and period may change depending upon the needs, over the range of about 5 to 40 mm Hg and 200 ms to 20 seconds.

Both LPP, pressure pulse generated by an external local apparatus (HEARTLESS PULSE), and BPP, the blood pressure pulse generated by the heart (HEART PULSE), cause local limb changes, which are measured with a plethysmograph, as noted above. To avoid overlap, LPP is timed to occur during diastole (the lower pressure flat part) of BPP; the invention detects the start of systole by seeking the time instant of maximum slope and identifying the start of diastole as 400 ms (typically; however based on heart rate) further in time from this time instant. LPP is allowed a period of 400 to 600 ms, and is terminated before the next systolic upswing.

Figure 6:
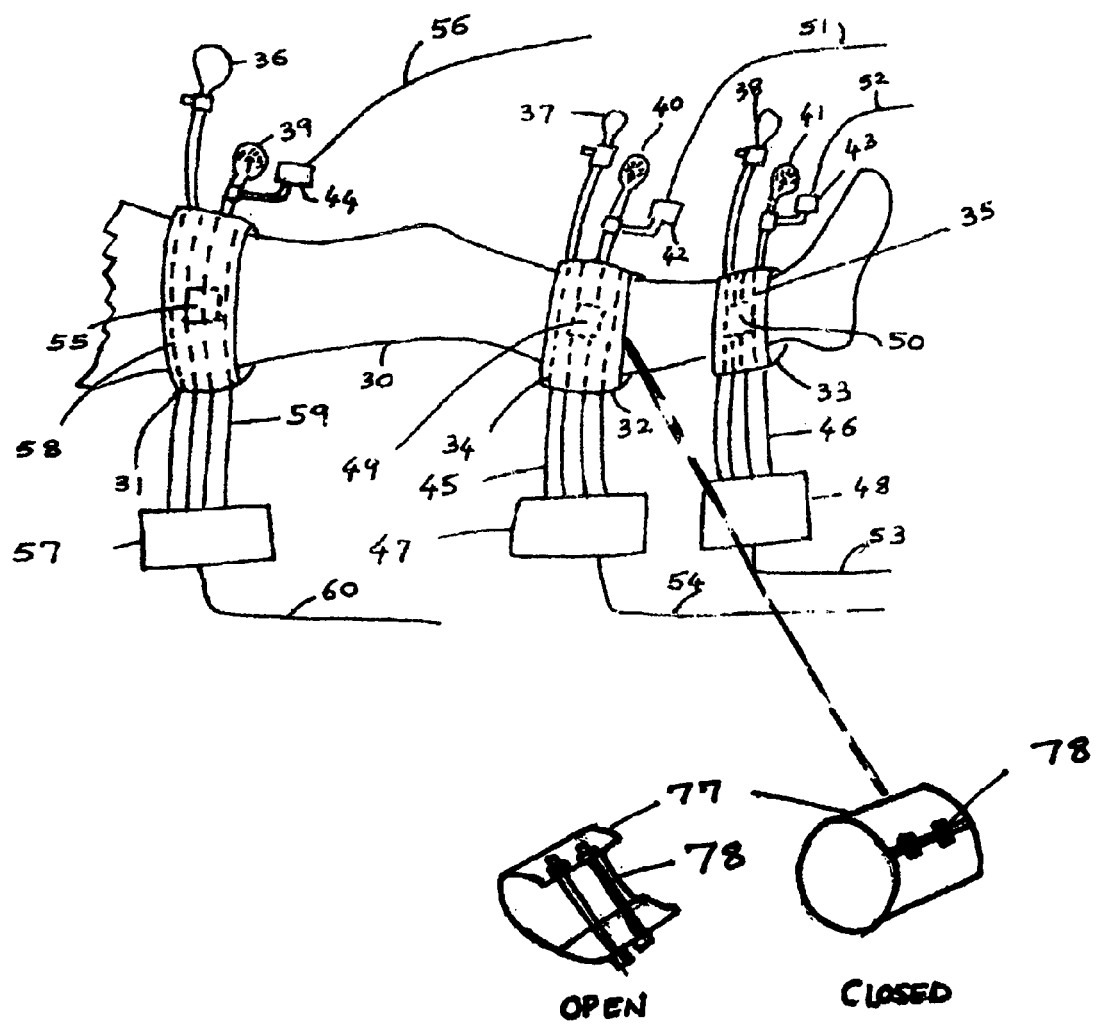
FIG. 6 is perspective views of a cuff with a stiff exterior.

Referring now to FIG. 6, a very useful modification ensues when any or all of the cuffs are changed to have a STIFF exterior (STIFF CUFF apparatus). This increases MLP signal amplitude by as much as 100%. This may be achieved with a thin (10 mil thick) sheet of stainless steel 77, for example, with screws 78 to tighten it around a limb cuff. The apparatus is shown in open and closed position, with it being in closed position when wrapped around a limb cuff, such as the intermediate cuff 32.

Referring now to FIGS. 7 and 8, means for administering a vasoactive drug to the leg 30 under a cuff 90 is shown. The cuff 90 is a conventional design with an inner layer 93, an inflatable bladder 92, and an outer layer 91. An absorbent pad 96 impregnated with the vasoactive drug, either a vasoconstrictor or a vasodilator, is positioned beneath the inner layer 93. A folded plastic film 94 impervious to the drug is positioned between the skin and the inner layer, with the upper half 95 extending past the lower half. When the drug to be administered to the skin surface, the exposed upper half 95 of the film is pulled out. As the film is removed, it slides against the cuff surface, but only rolls off the skin for minimal affecting of the skin. The absorbent pad is then applied directly to the skin to administer the drug. The upstanding pad 97 prevents the pad from sliding out as the film is removed. The pad may be removed by pulling on the upstanding end 97 when desired.

Operation of Invention

Figure 3:
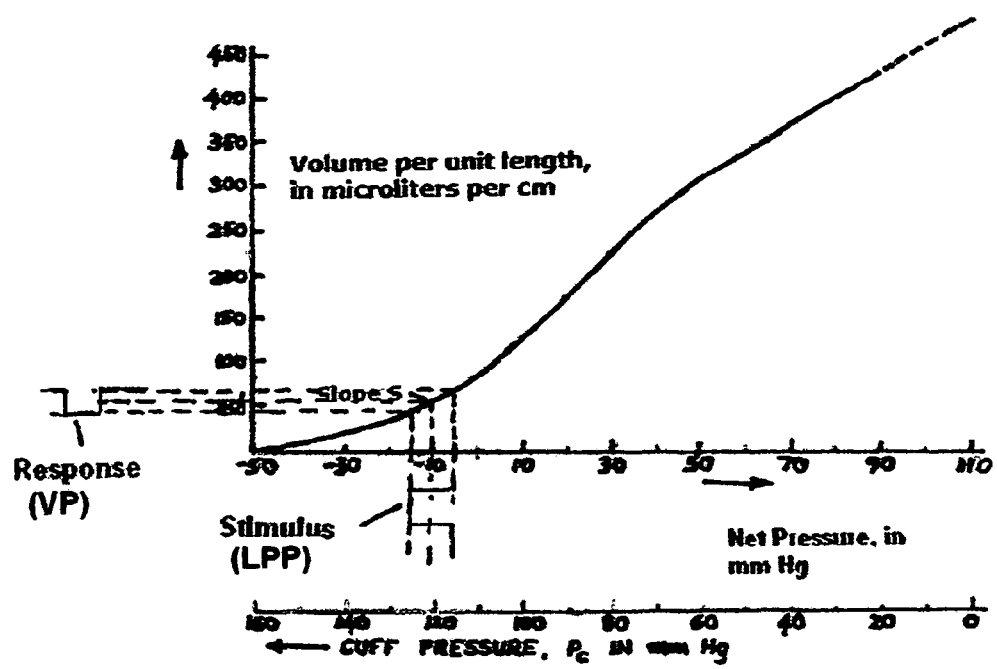
FIG. 3 shows a typical volume-pressure curve for use with the apparatus of FIG. 2

FIG. 3 shows a typical volume-pressure curve for an artery. The nonlinear plot is the consequence of the elastic constituents of the wall, viz., elastin, collagen, and smooth muscle cells. The decreasing slope at higher net (or transmural) pressures is due to increased involvement of collagen, while elastin is more involved at lower net pressures. Relaxation of smooth muscle would move the plot to left with increased slope in the 0 to 50 mm Hg range, while constriction would shift the plot to right with decreased slope in that pressure range, thus effectively creating a hysterisis type of loop.

The artery wall can be envisioned as having three types of control: the elastin-collagen complex which keeps the artery intact and small despite the high pressure—this is explained in more detail under THEORY OF OPERATION; functioning endothelium which can vasodilate or vasoconstrict the artery depending upon increased or decreased blood flow, respectively; and the smooth muscle cells which can change their degree of contraction under both global (neurologic) control and under local (endothelium mediated) control. A healthy artery utilizes these entire three phenomenons in regulating the artery lumen so blood flow to tissue is not compromised and can be shunted to the area of need quickly. It is this invention's goal to characterize these three factors in isolation and provide a combined measurement to gauge the health of the artery. Since atherosclerosis is a systemic disease, this invention uses limb arteries as it is known that atherosclerosis advances fairly rapidly in the leg arteries, concomitant with those in the heart and brain, while the arm arteries are spared of this disease progression. Thus, leg arteries can be studied to quantify the extent of atherosclerosis.

Figure 4:
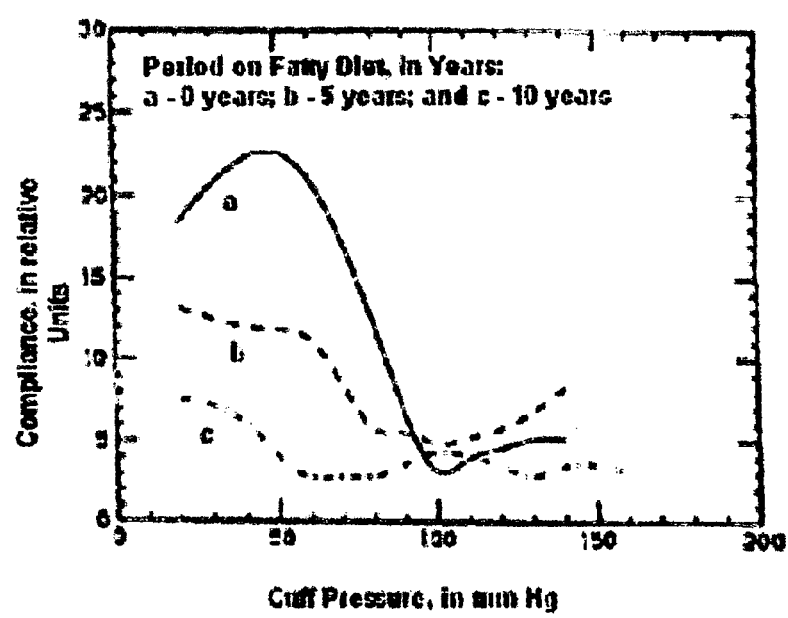
FIG. 4 depicts a typical compliance-pressure curve with disease progression.

FIG. 4 shows, based on my cross-sectional human studies and longitudinal monkey studies, a set of hypothetical plots that show how compliance, the slope of the volume-pressure curve, changes with period on fatty diet [U.S. Pat. No. 5,241,963]. The compliance plot is seen to peak less and reduce in amplitude with increased duration on atherosclerosis. This formed the basis for my earlier patents. This invention has extended this concept with two new parameters that quantify the impact of increased collagen content in the arterial wall, with advanced disease. However, atherosclerosis also may cause both endothelial dysfunction and smooth cell proliferation, both of which can lead to vasoconstriction and vasospasm as the hemodynamic system tries to optimize blood flow and fails, which causes further tissue damage; this leads to symptoms of pain, reduced capacity, or even sudden death.

First, methods based on the HEARTLESS PULSE apparatus are described.

Vulnerable Plaque Measures: An object is to increase the sensitivity of the peak compliance measurement—this is called the rigidity value; and to develop methods that can selectively target endothelium and smooth muscle cells for activation and inactivation—these measurements are called the dysfunction value and the contractility value, respectively. Another measurement, collagen value, is also measured; it is a structural-functional measurement. The HEARTLESS PULSE is ideally suited for all these goals, as described below. All these four parameters can be determined in multiple ways to evaluate plaque, and are respectively given the generic terms of rigidity value, autoregualtion value, contractility value, and collagen value.

Figure 10:
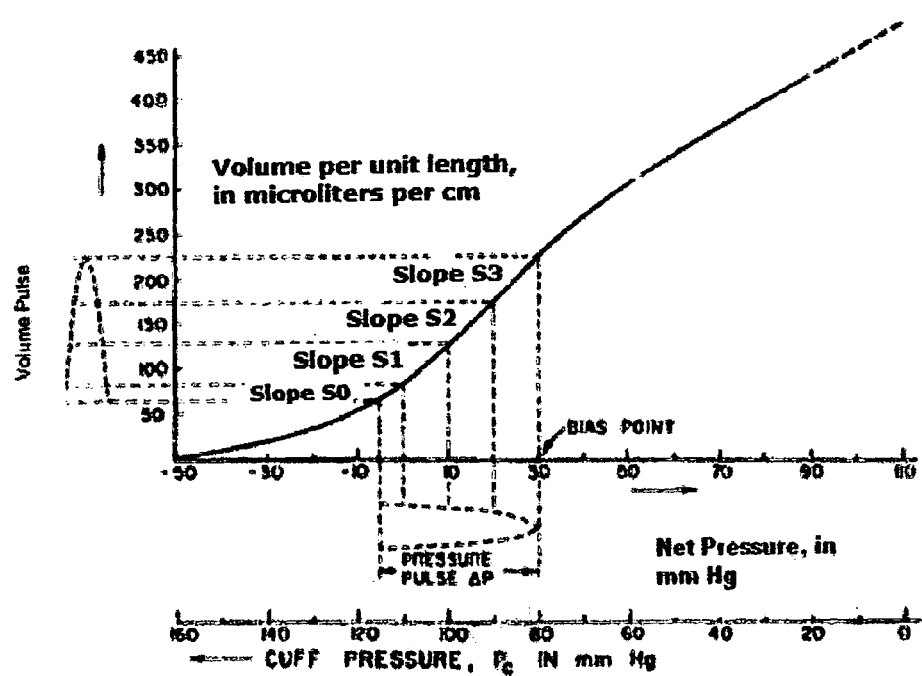
FIG. 10 depicts a typical volume-pressure curve for an artery for use with apparatus of FIG. 1.

Functional Measurement—rigidity value: This invention improves the sensitivity of the Peak Compliance measure [U.S. Pat. Nos. 5,343,867; 5,297,556; and 5,241,963]. HEARTLESS PULSE provides a significantly more sensitive measure. See FIG. 3 for HEARTLESS PULSE tracing and FIG. 10 for a HEART PULSE tracing, typical of prior art. Comparing them, note that the heart pulse, typically 40 mm Hg, traces a large part of the nonlinear volume-pressure curve. Thus, the derived compliance curve represents the average over a 40 mm Hg segment of the curve and inherently has a lower peak value when compared to the actual or real volume-pressure curve (the depicted plot was reconstructed from the recorded Plethysmographic signals, in response to the blood pressure pulse, BPP—thus it is not as steep as the actual or real volume-pressure curve). Thus, the first objective was to develop a methodology to generate pulses of 5 to 10 mm Hg amplitude to uncover the inherent higher slope and provide a more sensitivity peak compliance measure and compliance characteristic. The HEARTLESS PULSE apparatus provides this by externally generating this local pressure pulse, LPP. To avoid overlap with the pressure pulse generated from the heart, and to superimpose on a constant net pressure, this pulse is generated in the diastolic period of the blood pressure wave.

General Equation to compute volume pulse VP (see FIG. 5) from electrical limb pulse ELP is $$VP = [\rho \times L^2 \times ELP / R^2],$$

where $\rho$ is the blood resistivity=140 $\Omega$.cm, L is the length between the two inner voltage electrodes, in cm; ELP, the pulsatile output of the EP (electrical plethysmograph), in $\Omega$; and R is the tissue resistance, the DC output of EP, in $\Omega$. Both ELP and R are converted from the voltage readings to $\Omega$s, with the aid of a calibration coefficient for the given EP, obtained a priori, which is typically 10 to 100 mV/m$\Omega$. The calibration coefficient is a given constant to a given EP.

General Equation to compute volume pulse VP from mechanical limb pulse MLP is $$VP = MLP / \mathrm{CALIB},$$

where MLP is the ac output of the pressure transducer, in mm Hg, and CALIB is the pressure transducer output to a 1 ml calibration signal, in units of mm Hg/ml. CALIB is obtained for each patient-cuff wrapping and at each cuff pressure increment.

Option 1: Wrap the intermediate pressure cuff only, with the patient comfortably lying down. Use it with electrical plethysmograph (EP) 47. See FIGS. 1 and 2. Ensure that a good limb pulse is obtained; Use HEARTLESS PULSE or manual means to inflate to a preset pressure of about 100 mm Hg. Record the electrical limb pulse and identify the diastolic phase. Apply external pressure pulse of medium amplitude of about 20 mm Hg during diastole. Pulse is timed to occur during diastole, about 400 ms from the systolic upswing. Repeat this predetermined number of times, typically 30 to 60. This will increase blood flow by vasodilating the major arteries, in less than one minute. This also reduces the resistance pulse making the limb pulse a better predictor of the volume pulse; inflate the cuff to a pressure of about 200 mm Hg so ELP (electrical limb pulse) recorded is close to zero. Release the cuff pressure at a controlled rate (of about 2 mm Hg/s). Hold the cuff pressure at 10 mm Hg decrements; Generate an external local pressure pulse LPP of small amplitude, say 5 to 10 mm Hg, and period of 200 ms to 400 ms. Note the peak to peak amplitude of the LPP; Extract the ELP response, during the diastolic phase, to LPP. Discard the first few (say 5) recordings at a given cuff pressure. Average the next few (say five) to obtain the averaged limb pulse response signal. Call this ELP'; Repeat all this till the cuff pressure falls below 20 mm Hg; Note the ELP' with the maximum amplitude. Convert this to equivalent volume pulse, MVP ('Maximum Volume Pulse'). Note the corresponding cuff pressure, OCP ('Optimal Cuff Pressure). Peak Compliance, $C_{PK}$ is determined as the ratio of MVP to LPP. Compute the rigidity value as (10/$C_{PK}$). Also note the ELP' at a low cuff pressure of about 30 mm Hg, covert it to a volume pulse, RVP (resting volume pulse), and compute the resting compliance, $C_{RS}$ as the (RVP/LPP'), the corresponding external applied pressure. LPP and LPP' will most likely be the same value. The collagen value is calculated from the ratio of resting compliance to the peak compliance value.

Thus, for Option 1, rigidity value is given as RIGIDITY VALUE 1=10×LPP/MVP and the collagen value is given as COLLAGEN VALUE 1=10×[$C_{RS}/C_{PK}$] or 10×[RVP/MVP] if LPP and LPP' are approximately equal.

Option 2: Wrap an intermediate cuff on the lower leg. Use it as an electrical plethysmograph. Ensure good contact; Wrap a proximal cuff on the upper leg and increase the pressure to a value above the systolic pressure, so limb pulse in the intermediate cuff is zero. Wait for 10 to 20 seconds; Apply LPP, local pressure pulse, of low amplitude (about 10 mm Hg), and long duration (a period of 400 to 600 ms). Record the ELP, the electrical limb pulse. Convert ELP to volume pulse VP; Determine the Peak Compliance, $C_{PK}$, as the ratio of the VP to LPP; Increase the pressure in the intermediate cuff to a high value, say 100 mm Hg. Hold it for a preset time (say, about 3 minutes) and release. This will relax the smooth muscle in the vessel wall. An alternative to relax smooth muscle cells: Apply a transdermal patch. The patch contains an appropriate smooth muscle dilator, such as a Statin or Nitroglycerine. Wait for a preset time (of about 3 minutes); Apply LPP'. It may be different from LPP. Obtain the limb pulse ELP'. Deflate all cuffs. Compute VP' from ELP'. Determine $C'_{PK}$ as the ratio of VP' to LPP'; Find the CONTRACTILITY VALUE as (1−[$C_{PK}/C'_{PK}$])×10, or as (1−[ELP/ELP'])×10. The latter is acceptable if the two Pressure Pulse amplitudes, LPP and LPP', are about the same. RIGIDITY VALUE is then (10/$C'_{PK}$).

Thus, for Option 2, rigidity value is given by RIGIDITY VALUE 2=10×LPP'/VP'; and contractility value is given by CONTRACTILITY VALUE 1=(1−[$C_{PK}/C'_{PK}$])×10, or (1−ELP/ELP')×10.

Option 3: Wrap the proximal and intermediate pressure cuffs, with the patient comfortably lying down. See FIGS. 1 and 2. Ensure that a good limb pulse is obtained; Inflate the proximal cuff to a suprasystolic pressure so there is no limb pulse recorded. The arterial tree distal to this cuff will be at zero internal pressure; Generate an external pressure pulse of low amplitude, say 5 to 10 mm Hg, a long duration of about 1 to 20 seconds (this is called the HEARTLESS STEP function, the non-default option of HEARTLESS PULSE apparatus) and apply it to the intermediate cuff. See FIG. 2; Monitor the output of pressure transducer 42. Determine the time to reach the final value within 1% ('signal saturation'). Deflate all cuffs. Compute the compliance value (see below for more details); This will be the peak compliance, $C_{PK}$ of the artery. RIGIDITY VALUE is then computed as (10/$C_{PK}$). This value can be improved as with option 2, that is, smooth muscle cell relaxation, either with cuff inflation to a high pressure and release after 3 minutes, or use of a transdermal patch.

The signal processing to obtain the compliance assumes that the system response is second order, even if it is a higher order (see THEORY OF OPERATION). This is an acceptable approximation. One specific method is detailed below: Assume the square pulse is applied at time t=0; Compute the time for the pressure transducer output to saturate, say within 1 to 5%, call it T; Extract from the sampled and saved data, the normalized (normalized with respect to the final output value) values for t=T/4, T/2, and 3T/4. There are now four equations (for t=T/4, T/2, 3T/4, and T) of the form (from Doebelin, 1990, page 125):

Output=−A×$e^{Bt}$+C×$e^{Dt}$+1, where A, B, C, and D are given below: Let E=square root of ($\zeta^2$−1). Then A=[$\zeta$+E]/2E; B=(−$\zeta$+E)×$\omega_n$; C=[$\zeta$−E]/2E; and D=(−$\zeta$−E)×$\omega_n$. Find the best mathematical fit, using, say, Mathematica, for $\omega_n$ and $\zeta$. In terms of the model given in FIG. 11, $\omega_n$=1/square root of ($L_{eq}$×$C_{art}$) and $\zeta$=($R_{ext}$×$C_{art}$×$\omega_n$/2). Thus, calculate $C_{art}$, given a priori computed $L_{eq}$ and $R_{eq}$. The cross check should yield values within 10%.

Thus, for Option 3, rigidity value is calculated as RIGIDITY VALUE 3=10/$C_{art}$.

Regulatory Measurement—dysfunction value: Intact endothelium provides local control by adjusting the lumen of the artery to maintain shear rates and shear stress low, so flow is facilitated and the arterial wall is not stressed much. Average shear rate in an artery is calculated as (4×average blood velocity/radius of the artery). Thus, increased blood flow should lead to vasodilation, while decreased blood flow should lead to vasoconstriction. Endothelial dysfunction occurs both in stenotic sites and in angiographically normal coronary segments; consequently, local higher flow may actually lead to inappropriate vasoconstriction. FMD with reactive hyperemia has recently been shown not to be useful for evaluating endothelial functionality.

This invention stresses the artery locally with a proximal external pressure pulse (Thus, to stress the segment under the distal cuff, LPP is applied to the intermediate cuff, etc.). Assume that the generation is set to generate 10 mm Hg and short period of 200 ms. By doubling the pressure pulse height, the shear rate can be increased two fold. Similarly by halving the pressure pulse height, the shear rate can be reduced two fold. In addition, if the blood flow to the limb segment is arrested as with a proximal cuff maintained at a supra-systolic pressure, the radius of the artery segment reduces by 50%, and the artery compliance increases by a factor of 1 to 4. These steps will allow a wide range of shear rates (1 to 1000 $s^{-1}$) to be generated under controlled conditions. Representative shear rates in a femoral artery are in the range of 25 to 150 $s^{-1}$. Thus, sensitivity and specificity can be traded.

The details given below pertain to the use of the intermediate cuff to generate LPP and use of the distal cuff to record ELP or MLP (so, a generic LP is used in the details below). Inflate the intermediate cuff to about 40 mm Hg to collapse the veins; Inflate the distal cuff to about 30 mm Hg or less, depending upon whether it is to be used as MP or EP; Inflate the proximal cuff to about 200 mm Hg so no distal LP is recorded. Apply an external local pressure pulse of small amplitude (say 10 mm Hg), sPP. This will produce low shear rates in the distal segment. Note the distal limb pulse, mLP (minimum limb pulse).; Now, apply an external pressure pulse of large amplitude (say 40 mm Hg), lPP. This will produce large shear rates in the distal segment. Note the distal limb pulse, MLP (maximum limb pulse); Release or deflate all the cuffs; Compute the first value as (mLP/sPP). Compute the second value as (MLP/lPP). Compute the dysfunction value as (first value./second value)×10. Note that if endothelium is not functioning, there may not be a large difference between the two values.

Hence dysfunction value is calculated as DYSFUNCTION VALUE 1=[mLP/sPP]×[lPP/MLP]×10

Regulatory-Structural Measurement—contractility value: Smooth muscle cell proliferation forms the third aspect of the arterial wall that can cause sudden cardiac death, possibly due to vasospasm (significant contraction of the artery). Endothelial dysfunction allows a vasodilatory hormone, such as Serotonin, to become potently vasoconstrictive, due because of its direct effect on smooth muscles. Atherosclerosis causes smooth muscle cell proliferation. In combination or in isolation, both (Endothelial Dysfunction and Smooth Muscle Cell Proliferation) can cause vasospasm. Stress causes vasospasm to be uncovered; a transdermal patch of nitroglycerin vasodilates smooth muscle cells independent of endothelial functionality. Further, smooth muscle cells are sensitive to mechanical stretch, responding with equal and opposite force to a stretch. all these factors are advantageously combined. See option 2 under 'rigidity value.'

The second method is presented here. It uses left and right legs, as an example. Wrap an intermediate cuff on the left leg and determine Peak Compliance, as in Option 1 under 'rigidity value'; simultaneously wrap an intermediate cuff on the right leg and determine the peak compliance. There will be one modification, however: reduce the period of smooth muscle relaxation to ten seconds or less; Take the ratio of peak compliance of the right leg, $CR_{PK}$, to that of the left leg, $CL_{PK}$, ('Ratio'). CONTRACTITLITY VALUE is computed as (1−Ratio)×10.

Thus for Option 1, contractility value is computed as CONTRACTILITY VALUE 2=[1−($C_{RPK}/C_{LPK}$)]×10.

Vulnerable Blood and Vulnerable Myocardium measures: HEARTLESS PULSE is used in these measures. Shear rate is a measure of the velocity gradient across the lumen of a vessel. It is known that for normal persons, there is considerable (nonlinear) increase in viscosity at low shear rates, relative to that at high shear rates. This is due to the fact that red blood cells orient themselves in various directions, while near-stationary. However, with increased blood flow velocity and shear rate, the red blood cells tend to orient and shape themselves in the direction of flow, because of the flow dynamics. This reduces viscosity substantially. Diseased states may increase the blood viscosity at low shear rates by as much as 60% relative to healthy blood; this difference at higher shear rates reduces to 10%. Low shear rates occur near the blood-artery wall boundary even in normal flow, which may increase propensity for thrombus formation if the endothelium (the inner layer of the artery wall) is injured and, hence, dysfunctional. Low shear rate, and hence higher propensity for thrombus formation, occurs in veins which have low flow velocities and are fairly large in diameter. Since this does not occur in all people, the likely explanation is that blood-carried factors (lipids, proteins, blood cells, etc.,), that reflect injury and inflammation elsewhere, may instigate this. It may also occur on the arterial side when the flow is reduced due to high viscosity blood, and due to low flow regions created near a stenosis (narrowed artery lumen, due to plaque growth from the wall into the lumen), which in turn represent pathologic states. Thus, it is clear that study of viscosity at low shear rates, relative to that at high shear rates, can help uncover diagnostic information.

Fluid resistance, the ratio of pressure drop to flow velocity in a vessel, is directly proportional to viscosity. Thus, one can vary pressure (using HEARTLESS PULSE apparatus) and monitor downstream flow, to determine changes in viscosity. Another method is to apply a pressure pulse at a proximal site and determine the time of transit to a distal site. Neither of these techniques would have been possible without the ability to generate external pressure pulsations (of the HEARTLESS PULSE apparatus). However, the dynamic range is so large that, a simple method useful for long-term and daily monitoring can be developed using the HEART PULSE apparatus as well. The former are detailed below, while the latter is detailed later, under the HEART PULSE Methods.

The viscosity value: This invention varies the shear rate in a controlled manner through either an artery or a venous segment and measures the blood viscosity. Vulnerable blood shows a steeper drop in viscosity as shear rate is increased, while approaching the same value at higher shear rates, as blood from healthy persons. Ratio of pressure input to flow in the blood vessel may be used as a measure of viscous resistance and hence, viscosity, when the flow in the absence of the pressure input is zero. For the arterial side, the zero flow condition is obtained with a proximal cuff pressure sufficiently high to block arterial inflow. For the venous side, the flow is close to zero under normal conditions, that is, with no proximal occlusion, and a pressure pulse is applied in the opposite direction, that is, in the distal cuff, to produce forward venous flow.

Option 1—arterial viscosity value: Inflate the intermediate cuff to about 40 mm Hg, sufficient to collapse the venous segment; Inflate the distal cuff to about 30 mm Hg, spaced a predetermined distance (about 20 cm) away from the intermediate cuff. Use either EP or MP for the distal cuff; Inflate the proximal cuff to about 200 mm Hg so that distal limb pulse is close to zero; Generate a local external pressure pulse for the intermediate cuff. Set its amplitude, LPP, to be small (say 5 to 10 mm Hg). Note the arterial flow $F_a$ with a Doppler probe placed within a preset distance (say 5 cm) of the distal cuff, between the two cuffs. Determine the first clotting ratio as (LPP/$F_a$); Set the amplitude of the external pressure pulse, LPP', to be large (say 30 to 40 mm Hg). Note the arterial flow $F_a'$ with the Doppler probe as before; Deflate all the cuffs; Determine the second clotting ratio as (LPP'/$F_a'$). Compute the arterial viscosity value as, VISCOSITY VALUE 1=10×[first clotting ratio/second clotting ratio].

Option 2—venous viscosity value: Inflate the distal cuff to about 40 mm Hg. Inflate the intermediate cuff to about 30 mm Hg. Apply a local external pressure pulse, LPP, of low amplitude (say 5 to 10 mm Hg) to the distal cuff spaced a predetermined distance (about 20 cm) away from the intermediate cuff. Measure venous flow $F_v$ with a Doppler probe placed within a preset distance (say 5 cm) to the intermediate cuff, between the two cuffs. Determine the first clotting ratio as (LPP/$F_v$); Set the amplitude of the external pressure pulse, LPP', to be large (say 20 to 30 mm Hg). Note the venous flow, $F_v'$, with the Doppler probe as before. Deflate cuffs as appropriate; Determine the second clotting ratio as (LPP'/$F_v'$); Computer the venous viscosity value as, VISCOSITY VALUE 2=10×[first clotting ratio/second cloning ratio].

Option 3—Another way to measure viscosity value with the HEARTLESS PULSE apparatus: Inflate the intermediate cuff to 30 mm Hg. Inflate the distal cuff to about 30 mm Hg. Record both ELP and MLP from the distal cuff. Ensure intermediate and distal limb pulses can be recorded. Inflate the proximal cuff to a high pressure of about 200 mm Hg, so distal limb pulse is near zero. Apply an external local pressure pulse (LPP) of low amplitude (say 5 to 10 mm Hg) to the intermediate cuff and record ELP and MLP in the distal cuff. Convert them to equivalent volume pulse, $VP_E$ and $VP_M$, respectively. Take their peak amplitude difference as $RP_{low}$ (Resistance Pulse). Increase the LPP if no volume pulse is recorded, up to a maximum of about 30 mm Hg. The RP peak may not occur at the same peak as either of the ELP and MLP peaks. Repeat the measurement, with a larger external pressure pulse, LPP', say 30 to 40 mm Hg. Note the resistance pulse, $RP_{high}$. Compute viscosity value from VISCOSITY VALUE 3=10× $[RP_{low}/RP_{high}]$.

The propagation value: This invention is designed to measure propagation delay through the limb in a repeatable controlled manner. One can model the limb, for semi-quantitative purposes, as an RC model, with R representing the viscous resistance, and C, the arterial wall compliance. The time constant for pulse propagation can be estimated as RC. All the units are provided in the THEORY OF INVENTION. R changes from 10 to 1 mm Hg. $ml^{-1}$. s, as the shear rate increases from near zero to more than 300 $s^{-1}$. C changes from 5 to 25 μl. mm $Hg^{-1}$ as the net pressure inside the artery changes from 100 mm Hg to 0 mm Hg. Thus, under normal conditions, the RC value is 1×5 ms=5 ms, for a limb segment of about 10 cm length. Notice that this value can substantially change under different conditions. Higher viscosity can lead to delays of about 50 ms. At low pressures, this may increase to 250 ms. A large dynamic range for the propagation delay, thus, is evident. It can be used to uncover many related conditions, such as low blood pressure and high viscosity, which occur in atherosclerosis and diabetes. In addition, with the aid of a proximal cuff at a high pressure, dynamic range can be fully exposed.

The method follows: Place the proximal and distal cuffs at a predetermined distance of 25 to 50 cm along the limb. Inflate the proximal pressure cuff to a preset pressure. The preset pressure may be zero (this case is covered under the HEART PULSE option). The preset pressure may also be high, of the order of 100 to 200 mm Hg, depending upon the application. Inflate the distal cuff to a pressure of about 20 mm Hg. Use either electrical or mechanical plethysmograph for both the sites. Identify the diastolic phase with the aid of the proximal limb pulse. Generate an external local pressure pulse LPP of a predetermined amplitude (say 10 to 40 mm Hg). Note the limb pulse (LP) under the proximal and distal cuff. Deflate all the cuffs. Determine the time delay between the two LPs and average it. Note the distance between the cuffs. Compute the propagation value as, PROPAGATION VALUE 1=[time delay/distance]×1000.

Figure 9:
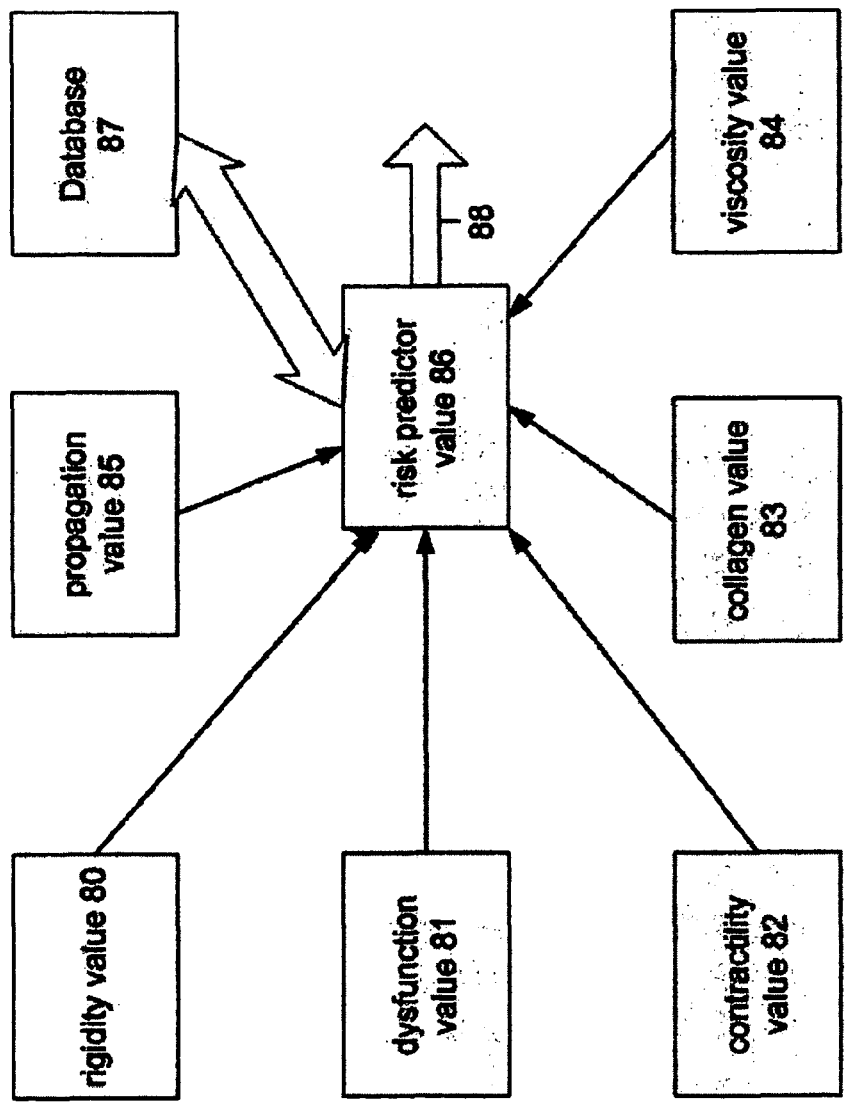
FIG. 9 shows a method for integrating the six types of measurements to obtain an overall risk predictor value.

Integrated value of Risk Prediction for Vulnerable Persons, the risk predictor value: See FIG. 9. The HEARTLESS PULSE mode is used to compute a measure each of rigidity value 80; dysfunction value 81; contractility value 82; collagen value 83, viscosity value 84, and propagation value 85. FIG. 9 shows how the six measurements, with typical values in the range of 1 to 20, with 1 being the healthiest score, can be combined, perhaps using a regression equation, as a weighted sum of the six measurements, to yield the integrated value, termed here risk predictor value 86 These can be compared to similar values for the arm for cross-sectional acute comparisons, or earlier values for the leg for individual longitudinal comparisons, or against similar values for the young and healthy patients for vulnerability comparisons, as existing in a database 87, which is updated from the latest set of values. Output 88 provides risk profile. The risk predictor value is computed as A×rigidity value+B×dysfunction value+ C×contractility value+D×collagen value+E×viscosity value+ F×propagation value, where the six parameter values on the right hand side are obtained from the measurements given above, and are typically in the range of 1 to 20. A, B, C, D, E, and F are constants derived from a database of healthy persons. The database of healthy persons further will provide two threshold values for each value category. A value lower than the lower threshold, say 30% of the maximum, is considered a healthy value; while a value higher than the higher threshold, say 70% of the maximum, is considered an advanced disease value. Thus, the risk predictor value higher than 70% of the maximum value may indicate advanced disease with heightened short-term risk of sudden cardiac death. One or more ways of obtaining the six parameter values have been provided above.

Methods that use HEART PULSE apparatus follow.

In FIG. 2, the HEARTLESS PULSE embodiment, an external local pressure pulse, LPP, is generated to analyze the hemodynamics of the local arterial segment. In the HEART PULSE apparatus, the heart generated pressure pulse, BPP, serves the purpose. Thus, the embodiment represented in FIG. 1 may be used. The methods below improve upon Shankar's earlier patents.

Functional Measurement—rigidity value: In this invention, the cuff pressure may also be decreased continuously, while the underlying limb pulse signal is acquired. This can be followed by a continuous increase in cuff pressure, to obtain one more set of recordings, so a better average is obtained. Protocol follows: Refer to FIG. 1. Measure the blood pressure in the arm or leg, using the standard Korotkoff method or the Oscillometric method. Determine the 'pressure pulse' BPP as the difference of the systolic and diastolic blood pressure. As an option, use the STIFF CUFF to enhance measurement accuracy; Wrap the intermediate pressure cuff only, with the patient comfortably lying down. Use it as an electrical (EP) or mechanical (MP) plethysmograph. Ensure that a good limb pulse is obtained; Relax the smooth muscle cells with the following procedure; Inflate to a Predetermined pressure (of about 100 mm Hg) and deflate quickly. Repeat this predetermined number of times, typically 5. This will increase blood flow by vasodilating the major arteries. This also reduces the resistance pulse making the limb pulse a better predictor of the volume pulse;

The actual data collection procedure can proceed in one of the four following manners: (a) Inflate the cuff to a pressure high enough (about 250 mm Hg) so no plethysmographic recording is discernible. Release the cuff pressure at a controlled rate of about 2 mm Hg/s Hold the cuff pressure at 10 mm Hg decrements. Wait for few (3 to 5) seconds for the signal to stabilize and obtain the signal over the ensuing few (3 to 5) seconds. Repeat this till the limb pulse signal, as recorded by MP, is no longer discernible (this happens when the cuff no longer makes good mechanical contact), or the cuff pressure falls below 20 mm Hg in the case of EP. (b) Inflate the cuff to a pressure high enough (about 200 mm Hg) so no plethysmographic recording is discernible. Release the cuff pressure at a controlled rate, say 0.5 to 1 mm Hg/s and obtain the signal at around pressure decrements of 10±2 mm Hg decrements; repeat as with option (a) till no discernible pulse. (c) Inflate the cuff at a controlled rate of about 2 mm Hg/s. Hold the cuff pressure at 10 mm Hg increments. Wait for few (3 to 5) seconds for the signal to stabilize and obtain the signal over the ensuing few (3 to 5) seconds. Repeat this till the cuff pressure reaches 200 mm Hg or the recorded plethysmographic signal is not discernible, whichever is lower. Deflate the cuff (d) Inflate the cuff at a controlled rate of 0.5 to 1 mm Hg/s and obtain the signal at around pressure increments of 10±2 mm Hg increments; repeat as with option (c) till no discernible pulse or the pressure of 200 mm Hg is exceeded, which ever occurs earlier. Deflate the cuff.

The data collection stage is followed by the data processing stage: Average the limb pulse signal; Note the limb pulse signal with the maximum amplitude. Convert this to equivalent volume pulse, MVP (maximum volume pulse). Note the corresponding cuff pressure (optimal cuff pressure); The peak compliance, $C_{PK}$ is determined as the ratio of the (MVP/BPP). The rigidity value is $(10/C_{PK})$; Note the limb pulse signal at a low cuff pressure (typically about of 30 mm Hg for the mechanical plethysmograph or a zero cuff pressure for the electrical plethysmograph). Convert this to equivalent volume pulse, RVP (resting volume pulse'). Calculate the resting compliance, $C_{RS}$ as (RVP/BPP). Calculate collagen value as either $(C_{PK}/C_{RS}) \times 10$ or (RVP/MVP)$\times 10$.

Thus, rigidity value is calculated as RIGIDITY VALUE 4=(BPP/MVP)$\times$10. The collagen value is calculated as COLLAGEN VALUE 2=$(C_{PK}/C_{RS}) \times 10$ or (RVP/MVP)$\times 10$.

Regulatory-Structural Measurement—contractility value: This involves obtaining the peak compliance from two limbs: for the first limb, smooth muscle cell relaxation is allowed, while for the second limb, it is not allowed with one exception for the second limb: no smooth muscle cell relaxation is allowed. To achieve this, the predetermined pressure is set to a high pressure (100 mm Hg) for the first limb and to a low pressure (0 to 10 mm Hg). Call the peak compliances obtained as $C_{PK1}$ and $C_{PK2}$, for the first and limbs, respectively. Then contractility value is obtained as $[1-(C_{PK2}/C_{PK1})] \times 10$.

Measures for vulnerable blood and vulnerable myocardium: HEART PULSE is used in this invention. One measure, propagation value, is described below.

Propagation value: Refer to the discussion under the HEARTLESS PULSE entry for propagation value. A suitable condition to discuss for the HEART PULSE option is the case where the proximal cuff pressure is set to zero. This may be needed when long term monitoring is the objective, and electrical plethysmography is used for measuring changes, especially in young diabetics, to monitor their daily glucose highs and lows. Failing myocardium, which may be coupled with high viscosity, also needs longer term monitoring This procedure addresses such needs. The procedure follows: use two EPs at no cuff pressure, or two MPs with cuff pressures at about 30 mm Hg, on a limb, separated by a predetermined distance, say 25 to 50 cm, to measure the propagation delay. Note the distance (Center to Center). Record the proximal and distal limb signals simultaneously; identify by signal processing the maximum slope time instant of the systolic upswing; Take the time difference. Determine the propagation value as, PROPAGATION VALUE 2=1000$\times$(time difference/distance).

Integrated value of Risk Prediction, the risk predictor value: This is computed and interpreted similar to the HEARTLESS PULSE apparatus (FIG. 9). Note, however, that two of the measures, viz., dysfunction value and viscosity value, are not available with the HEART PULSE apparatus.

Theory of Operation

Figure 11:
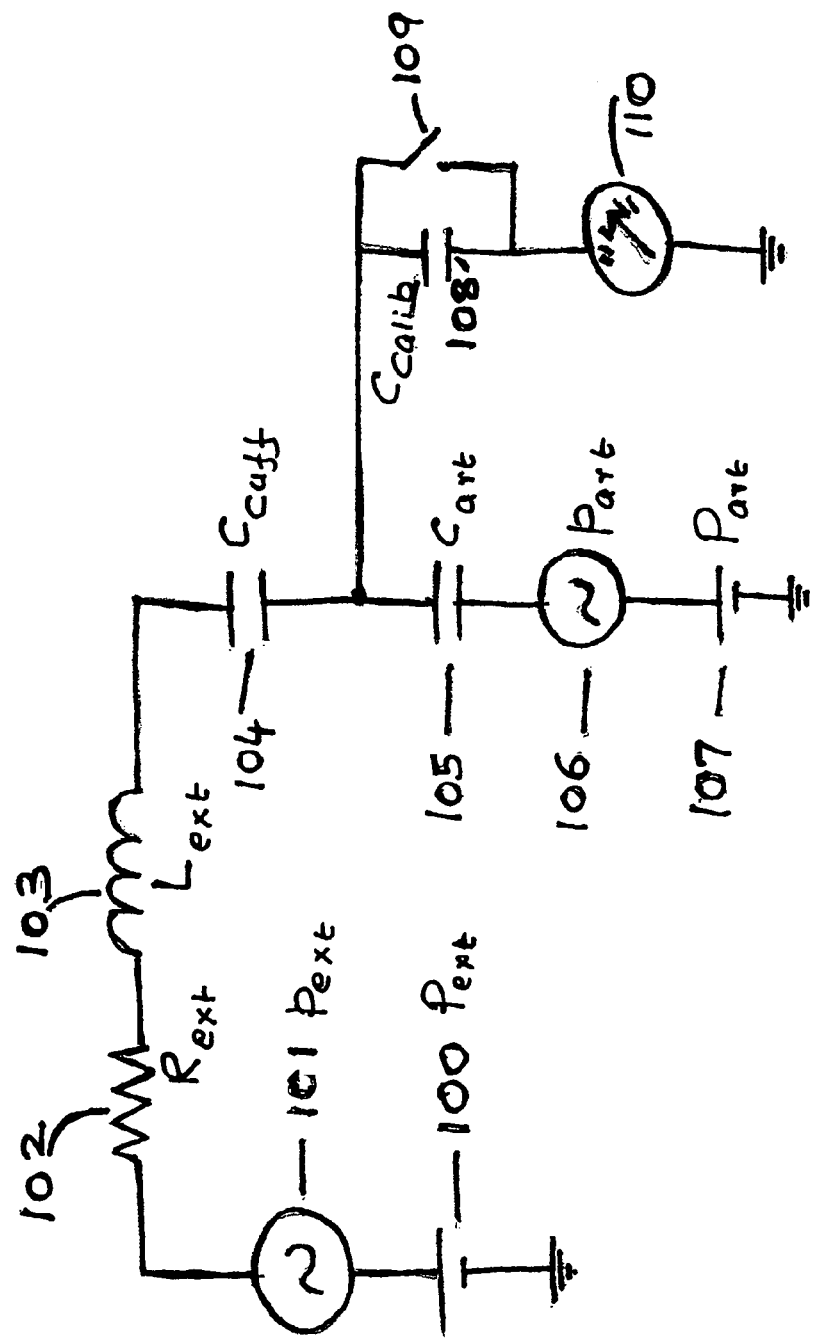
FIG. 11 is a diagram of an electrical analog of the pulsatile apparatus of FIGS. 1 and 2.

The Cuff Model: FIG. 11 shows a comprehensive cuff model that is essential to understand the HEARTLESS PULSE mode. $P_{ext}$, 100, and $p_{ext}$, 101, are the static and pulsatile components of the external pressure, respectively; $R_{ext}$, 102, and $L_{ext}$, 103, represent the viscous resistance and inertance due to a propagation through tubes and valves. These elements may also be intentionally introduced to characterize other unknown parameters; $C_{cuff}$, 104, is the compliance of the bladder-cuff combination; $C_{art}$, 105, is the compliance of the artery in the limb segment; $P_{art}$, 107, and $p_{art}$, 106, are the static and pulsatile components of the arterial pressure, that is, the diastolic pressure and pulse pressure, respectively; $C_{calib}$, 108, is the calibration chamber, typically 1 ml; 109 is a calibration button; and 110 is a pressure gage and it measures $P_{gage}$. Typical values for the compliances (in microliters/mm Hg) are: $C_{cuff}$-100; $C_{art}$-1 (at high net pressure) to 4 (at low net pressure); and $C_{calib}$-500. Typical values for the pressures (in mm Hg) are: $P_{art}$-80; $p_{art}$-40; $P_{ext}$-0 to 250; and $p_{ext}$-5 to 50 mm Hg. Prior art had no external pulsatile pressure component. Further, resistance and inertance may be ignored. Also, assume that switch across the calibration chamber is closed. Also assume that the static external pressure, that is the cuff pressure, is zero. Then it is easy to see, by analyzing the capacitance/compliance network, that the pressure gage would read 0.4 mm Hg when the artery compliance is 1 microliters/mm Hg. As an aside, if the cuff is made STIFF on the exterior, then $C_{cuff}$ will be reduced to, say, 50. This will increase the pressure gage reading to 0.8 mm Hg, thus enhancing the sensitivity substantially. If the external static pressure is increased to 100, the pressure gage would read a dc value of about 99, while the net pressure across the artery would be 99−80=19 mm Hg. This would actually increase the arterial compliance from 1 to 4 (because of the nonlinear volume-pressure curve), and the pressure gage would read a pulsatile pleasure of about 1.6 mm Hg. Reasoning so far validates this model as being appropriate for modeling the cuff-on-the-limb system.

Now, this model is extended to reason the effect of applying an external pressure pulse to the system. First assume that external resistance and inductance are zero. An external pulsatile pressure of 10 mm Hg will appear at the pressure gage as a 10 mm Hg pulse, with almost full amplitude, just as its static counterpart. Thus, the artery will experience the full 10 mm Hg amplitude. Now, by varying the external static pressure, one can trace the non-linear curve of the artery. If an electrical plethysmograph is used to monitor the limb pulse and hence the arterial volume, then taking the ratio of this to the pressure pulse as measured by the pressure gage gives the arterial compliance. As explained already, since the pressure pulse tracing the curve is much smaller in height, a truer representation of the volume-pressure curve can be obtained with the HEARTLESS PULSE apparatus. This invention will generate square pulses of computer controlled amplitudes (5 to 40 mm Hg) and periods (200 ms to 600 ms), the HEARTLESS SQUARE option. The computer controlled orifice 68 will have wider orifice for this application, say 0.3 to 1 cm in radius, with a length of 10 cm. For air, viscosity is 180 micropoise and density is 1.204 mg/ml [Cit. 2]. Using standard equations for calculation of resistance and inertance [Shanker, 1982, page 114], it can be shown that the resulting second order system (made up of $R_{ext}$, $L_{ext}$, and $C_{art}$) allows one to apply square pulse of the needed amplitude and period with good fidelity (under-to critically-damped system). The associated pressure transducer monitors this ac pressure pulse, while an electrical plethysmograph monitors the arterial volume change. Compliance is then calculated as the ratio of the latter to the former.

Now, if it is desired to avoid the use of an electrical plethysmograph, one can use computer control to reduce the size of orifice 68 to about 0.1 cm to 0.3 cm to control flow to the cuff and develop a calibration mechanism. This HEARTLESS STEP option generates a square pulse of about 10 mm Hg amplitude, but with a much longer period of 1 to 20 seconds. It is used to determine the arterial compliance by making it part of a second order system. For air, viscosity is 180 micropoise and density is 1.204 mg/ml [CRC, 1982]. Using standard equations for calculation of resistance and inertance [R, the viscous resistance, in mm Hg. $ml^{-1}.s$ is $(81/8)\times(\mu \times l)/((\pi \times r^4) \times 1333)$, where $\mu$ is the viscosity, in poise, l is the length of the section, in cm, r is the radius of the section, in cm, and L, the fluid inertance, in mm Hg. $ml^{-1}. s^2$ is $(9/4) (\rho \times l)/((\pi \times $r^2) \times 1333$), where $\rho$ is the density, in g. ml$^{-1}$], it can be shown that the second order system is over damped with a damping ratio ($\zeta$) of about 3 and above [Webster, 1998, page 31], as the artery compliance changes from 10 to 1 microliters/mm Hg [Shankar and Webster, 1991]. These are over damped system that require a $\omega n \times t$ period of 5 to 15 to reach the final value [Doebelin, 1990, pp. 125], or a time period of 1 to 20 seconds. With a few equal interval digital samples, say sampled at 10 samples per second, one can compute the corresponding arterial compliance values. To compute compliance from such time estimations requires that the value be determined a priori. They can be calculated with equations, as specified above, and/or by wrapping the cuff around tubing, such as acrylitic tubing of 2+cm radius, of known compliance with a value that is at least 10 times lower than that of the cuff. Compute $C_{art}$, given $R_{ext}$ and $L_{ext}$.

The invention claimed is:

1. Pulsatile measurement apparatus for application to a limb of a person, the apparatus comprising:
  at least one cuff selected from the group consisting of:
    a proximal pressure cuff for encircling a proximal portion of the limb,
    a distal pressure cuff for encircling a distal portion of the limb, and
    an intermediate pressure cuff for encircling a portion of the limb intermediate to the proximal and distal portions;
  at least one of the pressure cuffs provided with an inflatable bladder and cuff pressure system and means for generating external pressure pulses, with means for timing the pressure pulses to occur during diastolic phase of the person's blood pressure pulse;
  at least one of the pressure cuffs connected to a pressure bulb, a release valve, and an analog pressure gauge with an electronic pressure transducer providing electric signals indicative of pressure, with means for appropriate calibration;
  whereby mechanical plethysmographic measurements are made on output signals from pulse pressure;
  at least one of said pressure cuffs having four aluminum electrodes on the inside of the cuff, with electrical leads connected to the four electrodes, with said electrical leads providing electric plethysmographic output signals from pulse pressure; and
  signal processing means connected to the electric plethysmographic output signals and pressure transducer output signals from said pulse pressure for computing and displaying values relevant to conditions contributory to cardiac malfunction.

2. The apparatus of claim 1 in which the signal processing means is arranged to compute and display at least one of the values selected from the group consisting of rigidity value, dysfunctional value, contractility value, collagen value, viscosity value, and propagation value.

3. The apparatus of claim 1 further comprising: a transdermal patch positioned on at least one of the cuffs next to the skin of the person, the patch providing a drug selected from the group consisting of vasoconstrictors and vasodilators;
  means for initially preventing contact of the patch with the skin; and
  means for facilitating contact of the patch with the skin when required to elicit blood vessel response for measurement.

4. The apparatus of claim 1 in which at least one of the cuffs has an outer wall that is unyielding to thereby magnify pressure pulsations.

5. Pulsatile measurement apparatus for application to a limb of a person, the apparatus comprising:
  at least one cuff selected from the group consisting of:
    a proximal pressure cuff for encircling a proximal portion of the limb,
    a distal pressure cuff for encircling a distal portion of the limb, and
    an intermediate pressure cuff for encircling a portion of the limb intermediate to the proximal and distal portions;
  at least one of the pressure cuffs provided with an inflatable bladder and cuff pressure system and means for generating external pressure pulses, with means for timing the pressure pulses to occur during diastolic phase of the person's blood pressure pulse;
  at least one of the pressure cuffs having four aluminum electrodes on the inside of the cuff, with electrical leads connected to the four electrodes, with said electrical leads connected to the four providing electrical plethysmographic output signals from said pulse pressure;
  a transdermal patch positioned on at least one of the cuffs next to the skin of the person, the patch providing a drug selected from the group consisting of vasoconstrictors and vasodilators;
  means for initially preventing contact of the patch with the skin;
  means for facilitating contact of the patch with the skin when required to elicit blood vessel response for measurements; and
  signal processing means connected to the electric plethysmographic output signals from said pulse pressure for computing and displaying values relevant to conditions contributory to cardiac malfunction.

6. The apparatus of claim 5 in which the signal processing means is arranged to compute and display at least one of the values selected from the group consisting of rigidity value, dysfunctional value, contractility value, collagen value, viscosity value, and propagation value.

7. The apparatus of claim 5 in which at least one of the cuffs has an outer wall that is unyielding to thereby magnify pressure pulsations.

8. Pulsatile measurement apparatus for application to a limb of a person, the apparatus comprising:
  at least one cuff selected from the group consisting of:
    a proximal pressure cuff for encircling a proximal portion of the limb,
    a distal pressure cuff for encircling a distal portion of the limb, and
    an intermediate pressure cuff for encircling a portion of the limb intermediate to the proximal and distal portions;
  at least one of the pressure cuffs provided with an inflatable bladder and cuff pressure system and means for generating external pressure pulses, with means for timing the pressure pulses to occur during diastolic phase of the person's blood pressure pulse;
  at least one of the pressure cuffs connected to a pressure bulb, a release valve, and an analog pressure gauge with an electronic pressure transducer providing electric signals indicative of pressure, whereby mechanical plethysmographic measurements are made on output signals from pulse pressure; and
  signal processing means connected to the pressure transducer output signals from said pulse pressure for computing and displaying values relevant to conditions contributory to cardiac malfunction.

9. The apparatus of claim 8 in which the signal processing means is arranged to compute and display at least one of the values selected from the group consisting of rigidity value, dysfunctional value, contractility value, collagen value, viscosity value, and propagation value.

10. The apparatus of claim 8 further comprising: a transdermal patch positioned on at least one of the cuffs next to the skin of the person, the patch providing a drug selected from the group consisting of vasoconstrictors and vasodilators;
    means for initially preventing contact of the patch with the skin; and
    means for facilitating contact of the patch with the skin when required to elicit blood vessel response for measurement.

11. The apparatus of claim 8 in which at least one of the cuffs has an outer wall that is unyielding to thereby magnify pressure pulsations.

12. Pulsatile measurement apparatus for application to a limb of a person, the apparatus comprising:
    at least one cuff selected from the group consisting of: a proximal pressure cuff for encircling a proximal portion of the limb, a distal pressure cuff for encircling a distal portion of the limb, and
    an intermediate pressure cuff for encircling a portion of the limb intermediate to the proximal and distal portions;
    inflatable bladder and cuff pressure system and means for generating external pressure pulses, with means for timing the pressure pulses to occur during diastolic phase of the person's blood pressure pulse;
    at least one of the pressure cuffs connected to a pressure bulb, a release valve, and an analog pressure gauge with an electronic pressure transducer providing electric signals indicative of pressure, whereby mechanical plethysmographic measurements are made on output signals from pulse pressure; and
    signal processing means connected to the pressure transducer output signals from said pulse pressure for computing and displaying values relevant to conditions contributory to cardiac malfunction, in which the signal processing means is arranged to compute and display at least two of the values selected from the group consisting of rigidity value, contractility value, and propagation value.

13. The apparatus of claim 12 further comprising: a transdermal patch positioned on at least one of the cuffs next to the skin of the person, the patch providing a drug selected from the group consisting of vasoconstrictors and vasodilators;
    means for initially preventing contact of the patch with the skin; and
    means for facilitating contact of the patch with the skin when required to elicit blood vessel response for measurement.

14. The apparatus of claim 12 in which at least one of the cuffs has an outer wall that is unyielding to thereby magnify pressure pulsations.

15. The apparatus of claim 12 further comprising:
    at least one of the pressure cuffs having four aluminum electrodes on the inside of the cuff, with electrical leads connected to the four electrodes, with said electrical leads connected to the four providing electrical plethysmographic output signals from said pulse pressure; and
    signal processing means connected to the electric plethysmographic output signals from said pulse pressure for computing and displaying values relevant to conditions contributory to cardiac malfunction.

16. The apparatus of claim 15 further comprising a transdermal patch positioned on at least one of the cuffs next to the skin of the person, the patch providing a drug selected from the group consisting of vasoconstrictors and vasodilators;
    means for initially preventing contact of the patch with the skin; and
    means for facilitating contact of the patch with the skin when required to elicit blood vessel response for measurement.

17. The apparatus of claim 15 in which at least one of the cuffs has an outer wall that is unyielding to thereby magnify pressure pulsations.

18. Pulsatile measurement apparatus for application to a limb of a person, the apparatus comprising:
    at least one cuff selected from the group consisting of:
        a proximal pressure cuff for encircling a proximal portion of a limb;
        a distal pressure cuff for encircling a distal portion of the limb, and
        an intermediate pressure cuff for encircling a portion of the limb intermediate to the proximal and distal portions;
    at least one of the pressure cuffs having four aluminum electrodes on the inside of the cuff, with electrical leads connected to the four electrodes, with said electrical leads providing electrical plethysmographic output signals from said pulse pressure;
    a transdermal patch positioned on at least one of the cuffs next to the skin of the person, the patch providing a drug selected from the group consisting of vasoconstrictors and vasodilators;
    means for initially preventing contact of the patch with the skin; and
    means for facilitating contact of the patch with the skin when required to elicit blood vessel response for measurement; and
    signal processing means connected to the electric plethysmographic output signals from said pulse pressure for computing and displaying values relevant to conditions contributory to cardiac malfunction, in which the signal processing means is arranged to computer and display at least two of the values selected from the group consisting of rigidity value, contractility value, and propagation value.

19. The apparatus of claim 18 in which at least one of the cuffs has an outer wall that is unyielding to thereby magnify pressure pulsations.

* * * * *